United States Patent [19]

Heckert et al.

[11] 4,035,411
[45] July 12, 1977

[54] ORGANOSILANE COMPOUNDS

[75] Inventors: David C. Heckert, Oxford; David M. Watt, Jr., Cincinnati, both of Ohio

[73] Assignee: The Procter & Gamble Company, Cincinnati, Ohio

[21] Appl. No.: 570,537

[22] Filed: Apr. 22, 1975

[51] Int. Cl.² .......... C07F 7/10; C07F 7/18
[52] U.S. Cl. ............. 260/448.8 R; 260/448.2 N; 252/89 R; 252/541; 428/543
[58] Field of Search ........... 260/448.2 N, 448.8 R

[56] References Cited

U.S. PATENT DOCUMENTS

| | | | |
|---|---|---|---|
| 2,972,598 | 2/1961 | Morehouse | 260/448.8 R X |
| 3,389,160 | 6/1968 | Reid | 260/448.2 N |
| 3,471,541 | 10/1969 | Morehouse | 260/448.2 N X |
| 3,557,178 | 1/1971 | Golitz et al. | 260/448.8 R |
| 3,580,920 | 5/1971 | Culpepper | 260/448.8 R X |
| 3,624,120 | 11/1971 | Yetter | 260/448.2 N |
| 3,658,867 | 4/1972 | Prokai | 260/448.2 N |
| 3,661,963 | 5/1972 | Pepe et al. | 260/448.2 N |
| 3,817,739 | 6/1974 | Abbott et al. | 260/448.8 R X |
| 3,836,559 | 9/1974 | Prokai | 260/448.2 N |
| 3,898,257 | 8/1975 | Gregory | 260/448.8 R |

Primary Examiner—Paul F. Shaver
Attorney, Agent, or Firm—Charles R. Wilson; Robert B. Aylor; Richard C. Witte

[57] ABSTRACT

Novel compounds of the formula

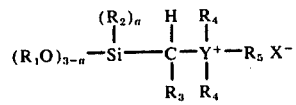

or siloxane oligomers thereof, wherein $R_1$ is an alkyl group containing 1 to 4 carbon atoms,

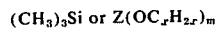

where $x$ is 2 to 4, $m$ is 1 to 20, Z is hydrogen, an alkyl group containing 1 to 18 carbons or an acyl group containing 1 to 4 carbon atoms; $a$ is 0 to 2; $R_2$ is an alkyl group containing 1 to 18 carbon atoms; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms,

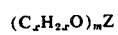

where $x$, $m$, and Z are as defined above, or oxygen provided only one $R_4$ is oxygen; $R_5$ is an alkyl, aryl or arylalkyl group containing 1 to 22 carbon atoms; X is halide; and Y is nitrogen, phosphorus or sulfur. The novel compounds are useful for inclusion in a detergent composition for imparting soil release benefits to metallic and vitreous surfaces contacted therewith.

13 Claims, No Drawings

ORGANOSILANE COMPOUNDS

BACKGROUND OF THE INVENTION

This invention relates to novel organosilane compounds.

Various quaternized substituted organosilane compounds are known. For example, British Pat. No. 686,068 discloses compounds having the general formula

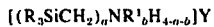

where R is an alkyl, monocyclic aryl hydrocarbon or alkoxy radical, $R^1$ is an alkyl, alicyclic hydrocarbon or monocyclic aryl hydrocarbon radical or hydroxy alkyl radical, $a$ is 1 to 2, $b$ is 0 to 3 with $a+b$ being not greater than 4 and Y is an acid anion. British Pat. No. 1,164,581 discloses compounds of the general formula

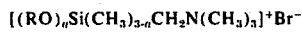

wherein R is an alkyl radical containing 1 to 6 carbon atoms or a phenyl radical and $a$ is 1 or 2. U.S. Pat. No. 3,730,701 discloses compounds of the formula

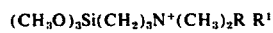

where R is an alkyl radical having 11 to 22 carbon atoms and $R^1$ is halide. These compounds are said to be useful as intermediates in the formation of organosilicon resins, catalysts and emulsifying agents (B. P. 686,068), as modifiers for organopolysiloxane resins and oils (B. P. 1,164,581) and for the control of algae (U.S. Pat. No. 3,730,701).

U.S. Pat. No. 3,560,442 discloses cross-linking agents of formula

where R is an alkyl radical having 1 to 4 carbon atoms, R' is hydrogen, an alkyl radical having 1 to 6 carbon atoms or a phenyl radical, R'' is hydrogen or a methyl radical and R''' is hydrogen, alkyl, cycloalkyl, aminoalkyl, (methylamino)-alkyl or (dimethylamino)-alkyl radical with 1 to 6 carbon atoms or a radical of formula $(RO)_3SiCH(R')-$ or $(RO)_3SiCH(R')N(R'')CH_2CH_2-$.

British Pat. No. 882,067 discloses compounds of formula

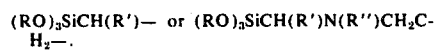

wherein R is a substituted or unsubstituted alkyl group, R' and R'' are hydrogen, or organic radicals, preferably alkyl, aminoalkyl, cyanoalkyl, hydroxyalkyl, carboalkoxyalkyl, carboxyalkyl or aryl radicals, or the monovalent grouping

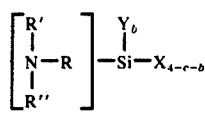

where X is an alkoxy radical or the oxygen atom of a siloxylidyne radical $\equiv Si - O -$, or R' and R'' together with the nitrogen atom may form a heterocylcic ring, Y is a hydroxy, alkoxy, alkyl or aryl radical, Z is an alkoxy, alkyl, or aryl radical, $c$ is 1 or 2, $b$ is 0 to 2, and $c+b$ is not more than 3.

It has now been found that the novel compounds as hereindescribed are useful as an additive to a detergent composition. Commonly assigned copending patent applications "Organosilane-Containing Detergent Composition" and "Organosilane-Containing Anionic Detergent Composition", both by Heckert and Watt, Ser. No. 570,534, filed Apr. 22, 1975 and Ser. No. 570,533, filed Apr. 22, 1975, respectively disclose detergent compositions containing a class of organosilanes. When metallic or vitreous surfaces are washed with a detergent composition containing the organosilane, a thin polymeric coating of the organosilane is deposited upon the washed or rinsed surfaces. The polymerized coating imparts a soil release benefit to the surface, thereby making the surface easier to clean in subsequent washings.

It is an object of this invention to produce novel organosilane compounds.

It is another object of this invention to produce organosilane compounds having utility in a detergent composition.

These and other objects will become apparent from the description to follow.

As used herein all percentages and ratios are by weight unless otherwise indicated.

SUMMARY OF THE INVENTION

An organosilane having the formula

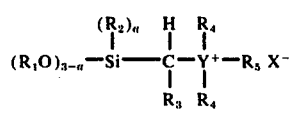

or siloxane oligomers thereof, wherein $R_1$ is an alkyl group containing 1 to 4 carbon atoms,

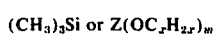

where $x$ is 2 to 4, $m$ is 1 to 20, Z is hydrogen, an alkyl group containing 1 to 18 carbons or an acyl group containing 1 to 4 carbon atoms; $a$ is 0 to 2; $R_2$ is an alkyl group containing 1 to 18 carbon atoms; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms,

where $x$, $m$, and Z are as defined above, or oxygen provided only one $R_4$ is oxygen; $R_5$ is an alkyl, aryl or arylalkyl group containing 1 to 22 carbon atoms; X is halide; and Y is nitrogen, phosphorus or sulfur.

DETAILED DESCRIPTION OF THE INVENTION

This invention relates to organosilane compounds having the formula

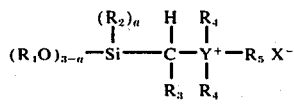

or siloxane oligomers thereof wherein $R_1$, $x$, $m$, $Z$, $R_2$, $a$, $R_3$, $b$, $R_4$, $R_5$, $Y$ and $X$ are as defined immediately above.

Preferably X is chloride or bromide, $a$ is 0 or 1, $R_3$ is a methyl group, $R_4$ is an alkyl group containing 1 to 4 carbon atoms and $R_5$ is an alkyl, aryl or arylalkyl group containing 6 to 12 carbon atoms.

It should be understood that the $R_4$ in the above formula and the formulae to follow may be the same or different. It should further be understood that when Y is sulfur, there will be only one $R_4$ substituent. Also, when one $R_4$ is oxygen or, under basic conditions, the anion of a carboxylic acid substituted alkyl, the counter ion $X^-$ is not extant. The 1 to 4 carbon atoms in the carboxy-substituted alkyl group is inclusive of the carboxyl group.

The preparation of the above compounds is described in the succeeding paragraphs.

The compounds when $a$ is 0 and $R_1$ is an alkyl group and $R_4$ is an alkyl, aryl or arylalkyl group are prepared by the following route:

slowly to the silane. The alpha-haloalkyltrihalosilane may be dissolved in an inert solvent, preferably hexane or pentane. (See W. Noll, "Chemistry and Technology of Silanes", Academic Press, New York, 1968, page 81 for the alcoholysis of halosilanes.)

One equivalent of the alpha-haloalkyltrialkoxysilane is reacted with one equivalent of the tertiary amine, tertiary phosphine, or dialkylsulfide to produce the organosilane. An inert solvent, preferably of high dielectric constant, may be used. The reaction is carried out at temperatures of from 40° C. to 100° C. and a time of 2 to 10 hours for the reaction of the bromopropyltrialkoxysilane and 120° C. to 140° C. for 2 to 20 hours for the reaction of the chloropropyltrialkoxysilane.

When $a$ is 1 or 2, the preparation of the compounds is essentially the same except for the use of an alkyl substituted silane as the starting reactant.

The organosilanes when at lease one $R_4$ is a carboxysubstituted alkyl group are prepared in the same manner except for the last reaction step. Here, a tertiary amine, tertiary phosphine or dialkylsulfide having a carboxy-containing alkyl group(s) is reacted with the alpha-haloalkyltrialkoxysilane at 50° C. to 200° C. for 2 hours to 20 hours. Such carboxysubstituted tertiary amines, tertiary phosphines, and dialkylsulfides are produced by reacting

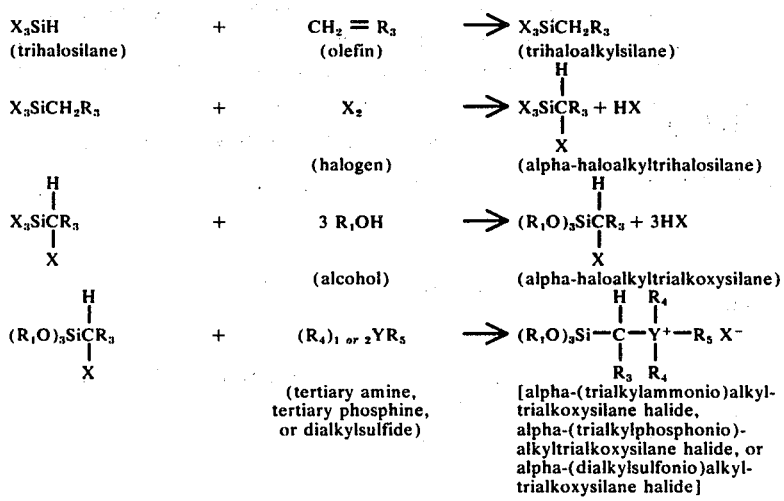

The trihalosilane is reacted with an olefin at 100° C. for 4 to 10 hours under a pressure of 50 to 300 psi. in the presence of a chloroplatinic acid or platinum catalyst to produce the trihaloalkylsilane. This reaction is reported by F. P. Mackay, O. W. Steward and P. G. Campbell in "Journal of the American Chemical Society, 79, 2764 (1957) and J. L. Speier, J. A. Webster and S. W. Barnes in Journal of the American Chemical Society, 79, 974 (1957).

The trihaloalkylsilane is then halogenated in a known manner by treating it with halogen in the presence of light (such as that provided by ordinary tungsten or fluorescent lamps). Preferably, halogenation is carried out to only partial completion and a distillation is performed to recycle unreacted alkylsilane.

The resultant alpha-haloalkyltrihalosilane is reacted with a lower alcohol to produce the alpha-haloalkyltrialkoxysilane. At least three equivalents of alcohol per equivalent of haloalkyltrihalosilane are added $R_4YHR_3$ or $HYR_5$ (where Y is sulfur)

with $X(CH_2)_{1-3}COOH$ in the presence of base at elevated temperatures, e.g. 50° C. to 150° C.

When at least one $R_4$ is $(C_xH_{2x}O)_mZ$ with $x$, $m$ and $Z$ as defined above, the compounds are produced in the manner given above except for the last reaction step. Thus, alpha-haloalkyltrialkoxysilane is reacted with a tertiary amine, tertiary phosphine, or dialkylsulfide where at least one substituent is $(C_xH_{2x}O)_mZ$ The reaction takes place at a temperature of 50° C. to 200° C. and a time of from 2 to 10 hours.

Organosilanes where one $R_4$ is oxygen are prepared by following the reactions outlined above up to the last reaction step. At this point, a dialkyl amine, dialkyl phosphine or alkylthiol is reacted with the halosilane at 50° C. to 200° C. for from 4 to 10 hours and then with base to produce an intermediate tertiary amine, phosphine, or dialkyl sulfide. These intermediates are then reacted with $H_2O_2$ at 20° C. to 100° C. or preferably $O_3$ in an inert solvent at −80° C. to 20° C. to yield the organosilane.

The compounds that follow are illustrative of these compounds $(C_2H_5O)_3SiCH(C_8H_{17})N^+(CH_3)_2C_{12}H_{25}$ $Cl^-$
$(CH_3O)_3SiCH(C_{18}H_{37})N^+(C_2H_4COOH)_2CH_3$
$(C_3H_7O)_2CH_3SiCH(C_{12}H_{25})N^+(C_2H_4OH)(CH_3)_2$ $Cl^-$
$(C_4H_9O)_3SiCH(C_3H_7)N^+[(C_2H_4O)_{10}H]_2C_6H_{13}$ $Br^-$
$(CH_3O)_3SiCH(C_{10}H_{21})N^+[_2H_4O)_2C_4H_9](CH_3)C_6H_5$ $Br^-$
$(CH_3O)_3SiCH(CH_3)N^+[(C_2H_4O)_3COC_2H_5](C_2H_5)_2$ $Br^-$
$(C_2H_5O)_2CH_3SiCH(C_8H_{17})N^+(O)^-(CH_3)_2$
$(CH_3O)_3SiCH(C_8H_{17})P^+(CH_3)_3$ $Cl^-$
$(CH_3O)_2CH_3SiCH(CH_3)P^+(C_3H_6COOH)_2C_{14}H_{28}C_6H_5$ $Cl^-$
$(C_2H_3O)_3SiCH(C_{10}H_{21})P^+(C_2H_4OH)C_4H_9$ $Cl^-$
$(CH_3O)_3SiCH(C_3H_7)P^+(O)^-(CH_3)C_{12}H_{25}$
$(CH_3O)_3SiCH(C_8H_{17})P^+[(C_2H_4O)_6H]_2CH_3$ $Cl^-$
$(C_2H_5O)_3SiCH(C_6H_{13})P^+[(C_3H_6O)_2C_{18}H_{37}](CH_3)_2$ $Cl^-$
$(CH_3O)_3SiCH(CH_3)S^+(CH_3)C_{16}H_{33}$ $Br^-$
$(C_2H_5O)_2CH_3SiCH(C_{12}H_{25})S^+(C_3H_6COOH)CH_3$ $Cl^-$
$(CH_3O)_2C_{16}H_{33}SiCH(C_2H_5)S^+(C_2H_4OH)C_2H_5$ $Cl^-$
$(CH_3O)_3SiCH(C_{10}H_{21})S^+(O)^-C_5H_{11}$
$(C_2H_5O)_3SiCH(C_4H_9)S^+[(C_3H_6O)_{10}H]C_6H_5$ $Cl^-$
$C_2H_5O)_3SiCH(CH_3)S^+[(C_2H_4O)_{20}C_2H_5]CH_3$ $Br^-$ when $R_1$ is $Z(OC_xH_{2x})_m$ the organosilane is formed in the same manner as the above compounds when $R_1$ is an alkyl group with the exception that $Z(OC_xH_{2x})_mOH$ is used in place of $R_1OH$ during the alcoholysis of the halosilane. This reaction takes place at 25° C. to 200° C. at 4 hours to 20 hours.

A mixture of $R_1OH$ and $Z(OC_xH_{2x})OH$ can be used in the alcoholysis step to prepare an organosilane having different substituents on the silicon atom.

The following compounds illustrate the organosilane when at least one $R_1$ is $Z(OC_xH_2)_m.$ $[CH_3(OC_2H_4)_3O]_3SiCH(CH_3)N^+(CH_3)_2C_{18}H_{37}$ $Cl^-$
$[C_2H_5(OC_2H_4)O]_2CH_3SiCH(C_2H_5)N^+(C_2H_4OH)_2C_{14}H_{29}$ $Cl^-$
$[H(OC_4H_8)_8O]_3SiCH(C_4H_9)N^+(C_2H_4COOH)(C_4H_9)CH_2C_6H_5$ $Cl^-$
$[CH_3CO(OC_2H_4)_2O]_3SiCH(C_2H_5)N^+(O)^-(CH_3)C_{10}H_{21}$
$[H(OC_3H_6)_6O]_3SiCH(C_{12}H_{25})N^+[(C_2H_4O)_{10}H]_2CH_3$ $Br^-$
$]C_{12}H_{25}(OC_2H_4)O]_3SiCH(C_3H_7)N^+[(C_4H_8O)_3C_5H_{11}](C_2H_5)_2$ $Cl^-$
$[C_{10}H_{21}(OC_2H_4)_4O]_3SiCH(C_2H_5)N^+[(C_2H_4O)_6COCH_3]_2CH_3$ $Cl^-$
$[H(OC_2H_4)_{16}O]_3SiCH(C_8H_{17})P^+(C_2H_5)_2C_6H_4C_4H_9$ $Cl^-$
$[CH_3(OC_2H_4)_{16}O]_2C_{12}H_{25}SiCH(CH_3)P^+(C_3H_6COOH)_2C_{10}H_{21}$ $Cl^-$
$[C_2H_5OC(OC_2H_4)_5O]_3SiCH(CH_3)P^+(C_2H_4OH)(CH_3)C_{12}H_{25}$ $Cl^-$
$[H(OC_2H_4)_2O]_3SiCH(C_{10}H_{21})P^+(O)^-(CH_3)C_{16}H_{33}$
$[H(OC_2H_4)_2O]_3SiCH(C_8H_{17})P^+[(C_2H_4O)_6H]_2C_4H_9$ $Br^-$
$[CH_3(OC_4H_8)_2O]_3SiCH(CH_3)P^+[(C_2H_4O)C_8H_{17}](CH_3)_2$ $Cl^-$
$[C_{10}H_{21}(OC_2H_4)_2O]_3SiCH(C_6H_{13})S^+(CH_3)C_{10}H_{21}$ $Cl^-$
$[H(OC_2H_4)_{14}O]_2C_2H_5SiCH(C_8H_{17})S^+(C_2H_4COOH)C_{18}H_{37}$ $Cl^-$
$[H(OC_3H_6)_4O]_3SiCH(C_{14}H_{29})S^+(C_4H_8OH)C_6H_5$ $Cl^-$
$[CH_3CO(OC_2H_4)_3O]_3SiCH(C_2H_5)S^+(O)^-C_{18}H_{37}$
$[C_{12}H_{25}(OC_2H_4)O]_3SiCH(C_3H_7)S^+[(C_3H_6O)H]C_6H_{13}$ $Cl^-$
$[H(OC_4H_8)_4O]_2CH_3SiCH(C_4H_9)S^+[C_2H_4O)_8C_3H_7]CH_3$ $Br^-$
$[H(OC_2H_6)_6O](C_2H_5O)_2SiCH(C_{12}H_{25})N^+[(C_2H_4O)_{10}H]_2C_{18}H_{37}$ $Br^-$
$[C_{14}H_{29}(OC_2H_4)_6O](CH_3O)_2SiCH(CH_3)P^+(C_3H_6COOH)_2CH_3$ $Cl^-$
$[H(OC_2H_4)_{10}O]_2(C_3H_7O)SiCH(C_5H_{11})S^+(CH_3)C_{12}H_{25}$ $Cl^-$ When $R_1$ is $(CH_3)_3Si$ and $a$ is 0, the compounds are prepared following the description given for the preparation of the above compounds with the exception that a tris(trimethylsiloxy)silane is used as the starting reactant. Commercially available trihalosilanes and trimethylsilanes are used to produce the starting reactant.

When $a$ is 1 or 2, a corresponding organosilane compound where one or two $R_1$'s are alkyl is reacted with a trimethylchlorosilane at about 50° C. to 200° C. to produce the desired organosilane.

Illustrative compounds follow:

$[(CH_3)_3SiO]_3SiCH(CH_3)N^+(CH_3)_2C_{18}H_{37}$ $Cl^-$
$[(CH_3)_3SiO]_2CH_3SiCH(C_2H_5)N^+(C_2H_4OH)_2C_6H_4CH_3$ $Cl^-$
$[(CH_3)_3SiO]_3SiCH(C_4H_9)N^+(C_3H_6COOH)(C_4H_9)_2$ $Cl^-$
$[(CH_3)_3SiO]_3SiCH(C_2H_5)N^+(O)^-(CH_3)C_{10}H_{21}$
$[(CH_3)_3SiO]_3SiCH(C_{12}H_{25})N^+[(C_2H_4O)_{10}H]_2CH_3$ $Br^-$
$[(CH_3)_3SiO]_3SiCH(C_3H_7)N^+[(C_4H_8O)_3C_5H_{11}](C_2H_5)_2$ $Cl^-$
$[(CH_3)_3SiO]_3SiCH(C_2H_5)N^+[(C_2H_4O)_6COCH_3]_2CH_3$ $Cl^-$
$[(CH_3)_3SiO]_3SiCH(C_8H_{17})P^+(C_2H_5)_2C_8H_{17}$ $Cl^-$
$[(CH_3)_3SiO]_2C_2H_5SiCH(CH_3)P^+(C_3H_6COOH)_2C_{10}H_{21}$ $Cl^-$
$[(CH_3)_3SiO]_3SiCH(CH_3)P^+(C_2H_4OH)(CH_3)C_{12}H_{25}$ $Cl^-$
$[(CH_3)_3SiO]_3SiCH(C_{10}H_{21})P^+(O)^-(CH_3)C_8H_{17}$
$[(CH_3)_3SiO]_3SiCH(C_8H_{17})P^+[(C_2H_4O)_6H]_2C_4H_9$ $Br^-$
$[(CH_3)_3SiO]_3SiCH(CH_3)P^+[(C_2H_4O)C_8H_{17}]_2C_6H_4C_2H_5$ $Cl^-$

[(CH₃)₃SiO]₃SiCH(C₆H₁₃)S⁺(CH₃)C₁₆H₃₃ Cl⁻
[(CH₃)₃SiO]₂SiCH(C₈H₁₇)S⁺(C₂H₄COOH)C₆H₅ Cl⁻
[(CH₃)₃SiO]₃SiCH(C₁₄H₂₉)S⁺(C₄H₈OH)CH₃ Cl⁻
[(CH₃)₃SiO]₃SiCH(C₂H₅)S⁺(O)⁻C₁₈H₃₇
[(CH₃)₃SiO]₃SiCH(C₃H₇)S⁺[(C₃H₆O)H]C₁₂H₂₅ Cl⁻
[(CH₃)₃SiO]₂C₁₈H₃₇SiCH(C₄H₉)S⁺[(C₂H₄O)₈C₃H₇]CH₃ Br⁻

Siloxane oligomers of the organosilanes are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably 2 to 20. A higher degree of polymerization adversely affects the ability of the compound to bond itself to a metallic or vitreous surface as discussed below and is for this reason avoided.

The above organosilanes are useful when used in a detergent composition at a level of organosilane to water-soluble organic detergent of from 2:1 to 1:10,000. When metallic or vitreous surfaces are washed or rinsed with a detergent composition containing the above-described organosilane, a soil release benefit is imparted to the surface. It is theorized that the positively charged organosilane is attracted to the negatively charged surface. The silicon atom in the organosilane can then form a bond with the surface. The presence of the positive charge on the organosilane is necessary to allow the bonding to take place from a dilute solution as is encountered in a detergent composition usage context and within a reasonable time period. The terminal alkyl groups attached to the positively charged atom provides the soil release benefits. It is believed that the organosilane compound polymerizes on the surface to form a thin coating of the polymer. The coating is responsible for imparting the soil release benefits to the surface. That is, a hard surface having on it the polymeric coating will be soiled; however, the soil is not tenaciously bound to the surface by virtue of the coating and for this reason is easily washed away.

The following examples illustrate this invention.

EXAMPLE I (CH₃O)₃SiCH(CH₃)N⁺(CH₃)₃ Br⁻

One mole (163.5g.) of ethyl trichlorosilane is placed in a one liter stirred Pyrex flask and irradiated with a 300 watt flood lamp. To this is added slowly, a cold mixture of ¼ mole of chlorine and ¼ mole of bromine so that a red-brown color is just maintained. When the addition is complete and the red color is gone, the residue is distilled out of the flask, yielding ½ mole of starting material, ethyltrichlorosilane and about ½ mole of alphabromoethyltrichlorosilane.

One-half mole of the alpha-bromoethyltrichlorosilane (121.25g.) is placed in a flask fitted with a stirrer, condenser, dropping funnel and a gas bubbler through which nitrogen is passed. 1.7 moles of absolute methanol (54.4g) are added slowly such that the reaction temperature does not rise above about 60° C.. When the methanol addition is complete and HCl evolution has ceased, the residue is distilled under reduced pressure to yield alpha-bromoethyltrimethoxysilane.

One quarter mole of the alpha-bromoethyltrimethoxysilane (57.3g) is placed in an autoclave along with 17.7g of trimethylamine. The mixture is heated to 80° C. for 6 hours under 200 p.s.i. nitrogen. The excess trimethylamine is allowed to evaporate after the product has been removed from the autoclave, leaving the bromide salt of alpha-trimethylammonioethyltrimethyoxysilane bromide.

Corresponding organosilanes where the nitrogen is phosphorus or sulfur are produced by substituting the trimethylamine with trimethylphosphine and dimethylsulfide, respectively.

EXAMPLE II

[(CH₃)₃SiO]₃SiCH(CH₃)N⁺(CH₃)₃ Br⁻

The product of the above reaction, trimethylammonioethyltrimethoxysilane bromide, is heated to reflux with an excess of trimethylchlorosilane until 3 equivalents of methylchloride is evolved. The resulting product, alpha-trimethylammonioethyl-tris-trimethylsiloxysilane bromide, is isolated by stripping out the residual volatile reactants.

EXAMPLE III (CH₃CH₂O)₃SiCH(C₄H₉)N⁺(CH₃)₂CH₂C₆H₅ Br⁻

In a manner like that used for the preparation of alpha-bromoethyltriethoxysilane, alpha-bromoamyltriethoxysilane is prepared in two steps from amyltrichlorosilane (commercially available). One-quarter mole of alpha-bromoamyltriethoxysilane (78.5g) is refluxed for 12 hours with 0.25 moles (33.75g) of benzyldimethylamine in 125 ml. of 2-butanone. The product, alpha-(benzyldimethylammonio)ethyltriethoxysilane bromide is isolated by removing the solvent under vacuum.

EXAMPLE IV (CH₃OCH₂CH₂O)₃SiCH(CH₃)N⁺(CH₂C-
H₂OCOCH₃)₂C₁₂H₂₅ Br⁻

One-quarter mole of alpha-bromoethyltrichlorosilane is dissolved in 200 ml. of dry hexane and sparged rapidly with nitrogen. 0.85 moles of the beta-methoxyethanol is added slowly and the resulting mixture is stirred until the HCl evolution ceases. Distillation of the residue yields alpha-bromoethyltris(beta-methoxyethoxy)silane. This produce (0.2 moles) is heated with 0.2 moles of the diacetate ester of dodecyldiethanolamine at 135° C. for 16 hours to yield the desired quaternary ammonium salt.

What is claimed is:
1. An organosilane having the formula

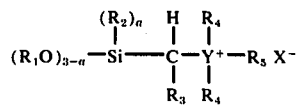

or siloxane oligomers thereof, wherein R₁ is an alkyl group containing 1 to 4 carbon atoms, (CH₃)₃Si or Z(OC$_x$H$_{2x}$)$_m$ where x is 2 to 4, m is 1 to 20, Z is hydrogen, an alkyl group containing 1 to 18 carbons or an acyl group containing 1 to 4 carbon atoms; a is 0 to 2; R₂ is an alkyl group containing 1 to 18 carbon atoms; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$, and Z are as defined above, or oxygen provided only one $R_4$ is oxygen and that when $R_4$ is oxygen, there is no $X^-$; $R_5$ is an alkyl, aryl or arylalkyl group containing 1 to 22 carbon atoms; X is halide; and Y is nitrogen, phosphorus or sulfur.

2. The organosilane of claim 1 wherein $R_1$ is an alkyl group.

3. The organosilane of claim 1 wherein $R_1$ is $$(CH_3)_3Si.$$

4. The organosilane of claim 1 wherein $R_1$ is $$Z(OC_xH_{2x})_m.$$

5. The organosilane of claim 1 wherein $a$ is 0 or 1.

6. The organosilane of claim 1 wherein the siloxane oligomer has a degree of polymerization of from 2 to 100.

7. The organosilane of claim 6 wherein the degree of polymerization is from 2 to 20.

8. The organosilane of claim 1 wherein the organosilane is a monomer.

9. The organosilane of claim 1 wherein X is chloride or bromide.

10. The organosilane of claim 1 wherein $R_3$ is methyl.

11. The organosilane of claim 1 wherein $R_4$ is an alkyl group containing 1 to 4 carbon atoms.

12. The organosilane of claim 1 wherein $R_5$ contains 6 to 12 carbon atoms.

13. The organosilane of claim 1 having the formula $$-\underset{R_3}{\underset{|}{Si}}\underset{}{\overset{(R_2)_n}{\overset{|}{{}}}}-\underset{R_4}{\underset{|}{C}}\overset{H}{\overset{|}{{}}}-\underset{}{\overset{}{N^+}}-R_5X^-\atop\underset{R_4}{}$$

or siloxane oligomers thereof, wherein $R_1$ is an alkyl group containing 1 to 4 carbon atoms, $(CH_3)_3$ Si or Z $(O\ C_x\ H_{2x})_m$ where $x$ is 2 to 4, $m$ is 1 to 20, Z is hydrogen, an alkyl group containing 1 to 18 carbon atoms or an acyl group containing 1 to 4 carbon atoms; $a$ is 0 to 2; $R_2$ is an alkyl group containing 1 to 18 carbon atoms; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

wherein $x$, $m$ and Z are as defined above, or oxygen provided only one $R_4$ is oxygen and that when $R_4$ is oxygen, there is no $X^-$; $R_5$ is an alkyl, aryl, or arylalkyl group containing 1 to 22 carbon atoms; and X is halide.

* * * * *

UNITED STATES PATENT AND TRADEMARK OFFICE
CERTIFICATE OF CORRECTION

PATENT NO. : 4,035,411

DATED : July 12, 1977

INVENTOR(S) : David C. Heckert and David M. Watt, Jr.

It is certified that error appears in the above-identified patent and that said Letters Patent are hereby corrected as shown below:

Column 5, line 21 "$(CH_3O)_3SiCH(C_{10}H_{21})N^+[_2H_4O)_2C_4H_9](CH_3)C_6H_5 \ Br^-$" should be -- $(CH_3O)_3SiCH(C_{10}H_{21})N^+[(C_2H_4O)_2C_4H_9](CH_3)C_6H_5 \ Br^-$ --.

Column 5, line 28 "$(C_2H_3O)_3SiCH(C_{10}H_{21})P^+(C_2H_4OH)C_4H_9Cl^-$" should be $(C_2H_5O)_3SiCH(C_{10}H_{21})P^+(C_2H_4OH)C_4H_9Cl^-$ --.

Column 5, line 37 "$C_2H_5O)_3SiCH(CH_3)S^+[(C_2H_4O)_{20}C_2H_5]CH_3Br^-$" should be -- $(C_2H_5O)_3SiCH(CH_3)S^+[(C_2H_4O)_{20}C_2H_5]CH_3Br^-$ --.

Column 6, line 6 "$]C_{12}H_{25}(OC_2H_4)O]_3SiCH(C_3H_7)N^+[(C_4$" should be -- $[C_{12}H_{25}(OC_2H_4)O]_3SiCH(C_3H_7)N^+[C_4$ --.

Column 7, line 2 "$[(CH_3)_3SiO]_2SiCH(C_8H_{17})S^+(C_2H_4COOH)C_6H_5Cl^-$" should be $[(CH_3)_3SiO]_2CH_3SiCH(C_8H_{17})S^+(C_2H_4COOH)C_6H_5Cl^-$ --.

UNITED STATES PATENT AND TRADEMARK OFFICE
CERTIFICATE OF CORRECTION

PATENT NO. : 4,035,411
DATED : July 12, 1977
INVENTOR(S) : David C. Heckert and David M. Watt, Jr.

It is certified that error appears in the above-identified patent and that said Letters Patent are hereby corrected as shown below:

Column 10, line 12

"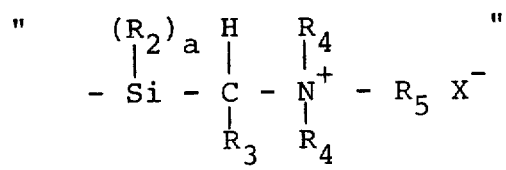"

should be

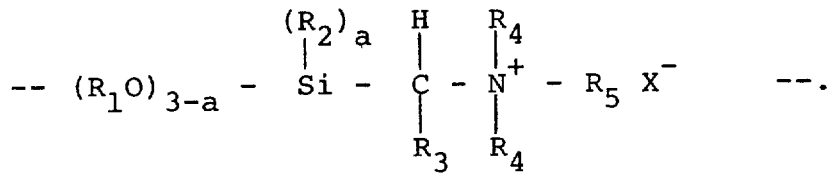  --.

Signed and Sealed this

Fourteenth Day of November 1978

[SEAL]

Attest:

RUTH C. MASON
Attesting Officer

DONALD W. BANNER
Commissioner of Patents and Trademarks